(12) United States Patent
Tan et al.

(10) Patent No.: US 8,546,614 B1
(45) Date of Patent: Oct. 1, 2013

(54) MULTIFUNCTIONAL CROSSLINKERS FOR SHAPE-MEMORY POLYIMIDES, POLYAMIDES AND POLY(AMIDE-IMIDES) AND METHODS OF MAKING THE SAME

(75) Inventors: Loon-Seng Tan, Centerville, OH (US); David Huabin Wang, Beavercreek, OH (US)

(73) Assignee: The United States of America as represented by the Secretary of The Air Force, Washington, DC (US)

( * ) Notice: Subject to any disclaimer, the term of this patent is extended or adjusted under 35 U.S.C. 154(b) by 0 days.

(21) Appl. No.: 13/557,326

(22) Filed: Jul. 25, 2012

Related U.S. Application Data

(60) Provisional application No. 61/636,134, filed on Apr. 20, 2012, provisional application No. 61/636,170, filed on Apr. 20, 2012.

(51) Int. Cl.
*C07C 211/54* (2006.01)

(52) U.S. Cl.
USPC .......................................... 564/305; 564/315

(58) Field of Classification Search
USPC ................................................. 564/305, 315
See application file for complete search history.

(56) References Cited

U.S. PATENT DOCUMENTS

| | | | |
|---|---|---|---|
| 3,455,879 A | 7/1969 | Gay et al. |
| 3,835,120 A | 9/1974 | Bach et al. |
| 4,107,125 A | 8/1978 | Lovejoy |
| 4,271,288 A | 6/1981 | Woo |
| 4,394,499 A | 7/1983 | Robinson et al. |
| 4,728,697 A | 3/1988 | Bolon et al. |
| 4,981,497 A | 1/1991 | Hayes |
| 5,101,037 A | 3/1992 | McGrath et al. |
| 5,175,234 A | 12/1992 | Lubowitz et al. |
| 6,307,008 B1 | 10/2001 | Lee et al. |
| 6,509,094 B1 | 1/2003 | Shah et al. |
| 2006/0217482 A1 | 9/2006 | Lukehart et al. |

OTHER PUBLICATIONS

Straub, Daniel. Lewis Structures of Boron Compounds Involving Multiple Bonding. Journal of Chemical Education. 72(6), (1995), 494-497.*
Chao, Tsung-Yi. Nonlinear optical polyimide/montmorillonite nanocomposites consisting of azobenzene dyes. Dyes and Pigments. 77 (2008) 515-524.*
St. Clair, Anne K., et al. "Synthesis and Characterization of Essentially Colorless Polyimide Films," J. Polym. Mater. Sci Eng., vol. 51, pp. 62-66 (1984).
Miner, Gilda A., et al, "The Wettability of LaRC Colorless Polyimide Resins on Casting Surfaces," J. Polym. Mater. Sci Eng., vol. 76, pp. 381-382 (1997).
Makita, Shohei, et al., "Synthesis of Alkaline-Developable, Photosensitive Hyperbranched Polyimides through the Reaction of Carboxylic Acid Dianhydrides and Trisamines," Journal of Polymer Science Part A: Polymer Chemistry, vol. 42, 3697-3707 (2004).
Lendlein Andreas et al., "Shape-Memory Polymers," Angewandte Chemie, International Edition, vol. 41, 2034-2057 (2002).
Liu C. et al, "Review of Progress in Shape-Memory Polymers," Journal of Materials Chemistry, vol. 17, 1543-1558 (2007).
Fay, Catherine C. et al., "Molecularly Oriented Polymeric Thin Films for Space Applications," High Performance Polymers, vol. 11, 145-156 (1999).
SRS Technologies and Mantech Materials, "Polyimides: CP1 and CP2 Film Properties," printed Jul. 9, 2012, 1 page, available at <http://www.mantechmaterials.com/_images/documents/3_8_doc.pdf>.
Wang, D.H., et al., "Photomechanical Response of Glassy Azobenzene Polyimide Networks," Macromolecules 2011, 44, pp. 3840-3846.
Pyun, Eumi, et al., "Kinetics and mechanisms of thermal imidization of a polyamic acid studied by ultraviolet-visible spectroscopy", Macromolecules (1989), 22(3), 1174-83.
Hosono, Nobuhiko, et al., "Photochemical control of network structure in gels and photo-induced changes in their viscoelastic properties" Colloids and Surfaces, B: Biointerfaces (2007), 56(1-2), 285-289.
Zhang, Chaohui, et al., "Rapid bending of a nonliquid crystal azobenzene polymer film and characteristics of surface relief grating" Journal of Applied Polymer Science (2009), 113(2), 1330-1334.
Hergenrother, P.M., "Recent Developments in High Temperature Organic Polymers," Polyimides and Other High-Temperature Polymers, Abadie, M.J.M. and Sillion, B., Eds., Elsevier: New York, 1991, pp. 1-18.
Agolini, F., et al., "Synthesis and Properties of Azoaromatic Polymers," Macromolecules (May-Jun. 1970), vol. 3, No. 3, 349-351.
White, T.J., et al., "A high frequency photodriven polymer oscillator," J. Soft Matter 2008,4, 1796-1798.
White, T.J., et al., "Polarization-controlled, photodriven bending in monodomain liquid crystal elastomer cantilevers," J. Mater. Chem. 2009, 19, 1080-1085.
Lee, K.M., et al., "Relationship between the Photomechanical Response and the Thermomechanical Properties of Azobenzene Liquid Crystalline Polymer Networks," Macromolecules 2010, 43, 8185-8190.
Sroog, C.E., "Polyimides," Prog. Polym. Sci. 1991, 16, 561-694.
Koshiba, Y., et al., "Photo-induced alignment behavior of azobenzene compound in thin film," Thin Solid Films 2009, 518, 805-809.
Koerner, H., et al., "Photogenerating work from polymers," Mater. Today (Oxford, U. K.) 2008, 11, (7-8), 34-42.
Wang, D.H., et al., "Nanocomposites Derived from a Low-Color Aromatic Polyimide (CP2) and Amine-Functionalized Vapor-Grown Carbon Nanofibers: In Situ Polymerization and Characterization," Macromolecules 2007, 40, 6100-6111.
Arlen, M., et al., "Thermal-Electrical Character of in Situ Synthesized Polyimide-Grafted Carbon Nanofiber Composites," Macromolecules 2008, 41, 8053-8062.

(Continued)

*Primary Examiner* — Samantha Shterengarts
(74) *Attorney, Agent, or Firm* — AFMCLO/JAZ; Rebecca Greendyke

(57) ABSTRACT

Multifunctional amine crosslinkers that may be used to create crosslinked polyimide, polyamide, and poly(amide-imide) polymers and films having shape memory properties at elevated temperatures and methods of making the same.

1 Claim, 2 Drawing Sheets

(56) References Cited

OTHER PUBLICATIONS

Lee, Kyung Min, and White, Timothy J., "Photomechanical Response of Composite Structures Built from Azobenzene Liquid Crystal Polymer Networks," Polymers (2011), 3, 1447-1457.

Behl, Marc, et al., "Shape-memory polymers" Materials Today (Oxford, United Kingdom) (2007), 10(4), 20-28.

Xie, Tao, "Recent advances in shape memory polymer," Polymer (2011), 52(22), 4985-5000.

Liu, C., et al., "Review of progress in shape-memory polymers," Journal of Materials Chemistry (2007), 17(16), 1543-1558.

Koerner, Koerner, et al., "Polymer design for high temperature shape memory: Low crosslink density polyimides," Polymer(2013), 54, 391-402.

Shumaker, J.A., et al, "Synthesis of high temperature polyaspartimide-urea based shape memory Polymers," Polymer (2012), 53, 4637-4642.

Jeong, K.U., et al., "Adhesion property of novel polyimides containing fluorine and phosphine oxide moieties" J. Adhesion Sci. Technol., vol. 15, No. 14, pp. 1787-1803 (2001).

Whitaker, Craig M., et al., "Synthesis and Solid-state Structure of Substituted Arylphosphine Oxides," Journal of Organic Chemistry (1995) 60, 3499-3508.

Sinou, Denis, et al., "Synthesis of a Family of Triarylphosphanes with Fluorous Phase Affinity," European J. Org. Chem. 2002, 269-275.

Schuh, Christian, et al., "Shape-Memory Properties of Segmented Polymers Containing Aramid Hard Segments and Polycaprolactone Soft Segments," Polymers 2010, 2, 71-85.

Rabani, Gouher, et al., "Synthesis and characterization of two shape-memory polymers containing short aramid hard segments and poly(3-caprolactone) soft segments," Polymer (2006) 47, 4251-4260.

* cited by examiner

MULTIFUNCTIONAL CROSSLINKERS FOR SHAPE-MEMORY POLYIMIDES, POLYAMIDES AND POLY(AMIDE-IMIDES) AND METHODS OF MAKING THE SAME

CROSS-REFERENCE TO RELATED APPLICATIONS

This application is related to, and claims priority from, co-pending U.S. Provisional Patent Application No. 61/636,134, filed on Apr. 20, 2012, by inventor Loon-Seng Tan, et al., and entitled "Multi(Azobenzene-Amine) Photo-Active Crosslinkers," and co-pending U.S. Provisional Patent Application No. 61/636,170, filed Apr. 20, 2012, by inventor Loon-Seng Tan, et al., and entitled "Azobenzene-Containing Glassy Polyimides Capable of Photo-Induced Large-Angle Bending," both of which are incorporated herein by reference in their entirety.

RIGHTS OF THE GOVERNMENT

The invention described herein may be manufactured and used by or for the Government of the United States for all governmental purposes without the payment of any royalty.

BACKGROUND OF THE INVENTION

1. Field of the Invention

This invention relates generally to the field of multifunctional crosslinkers. More particularly, it relates to tri- and tetrafunctional amine crosslinkers that may be used to create crosslinked polyimide, polyamide, and poly(amide-imide) polymers and films having shape memory properties at elevated temperatures and methods of making the same.

2. Description of the Related Art

Shape memory materials, including shape memory polymers (SMPs) and shape memory alloys (SMAs) are a class of active materials that can be programmed to "fix" a temporary shape or a series of temporary shapes and to recover to a "memorized" permanent shape upon application of a predetermined external stimulus. The permanent shape of most SMPs is established during the manufacturing process by a network of covalent or physical crosslinking. While the shape memory effects of SMAs stem from martensitic/austenitic transitions (changes in crystal structure), the shape memory effect of thermally-induced SMPs is driven by heating the polymer above its glass transition temperature ($T_g$) or melting point ($T_m$), which causes the SMP to become soft and elastomeric in nature. The heated SMP may be deformed into one or more temporary shapes. The SMP is then cooled below the $T_g$ or $T_m$ while still under stress, causing immobilization of the constituent network chains to fix the temporary shape. Recovery of the permanent shape is then accomplished by heating the SMP above the $T_g$ or $T_m$ which remobilizes the network chains and allows rubber (entropic) elasticity to return the SMP to its equilibrium or permanent shape. Other types of SMPs include light-induced, electro-active, pH-responsive, and water/moisture-driven SMPs.

SMPs and SMAs have been widely used in actuation, robotics, and piping, as components in aircraft and automobiles, and in medical and dental applications. SMPs possess many properties that make them more attractive than SMAs, such as much lower cost, easier manufacturing and processing using conventional methods, higher capacities for elastic deformation (up to 200% in most cases), lower density, and a broader range of customizable application temperatures. In addition, many SMPs have the potential for biocompatibility and biodegradability. However, most currently available SMPs consist of high-alkyl content polymers such as polyurethane, poly(ε-caprolactone), poly(norbornene), (ethylene-oxide)/(ethylene terephthalate)-based copolymers, styrene/butadiene copolymers, thiolene/acrylate copolymers, etc. Many of these SMPs do not possess shape memory properties above 150° C., nor do they possess long-term thermal and thermo-oxidative stability in this temperature region.

Aromatic polyimides, polyamides, and poly(amide-imides) are common classes of heat-resistant, thermally stable polymers with glass-transition temperatures in the excess of 150° C. The solubility of the polymers in common organic solvents may be improved by introducing wholly aromatic groups containing meta-phenoxyphenol ($-OC_6H_4-OC_6H_5$) or meta-oxyphenylene-meta-oxyphenoxy ($-OC_6H_4O-C_6H_4O-$) moieties to the main chains or side chains of the polymer backbones. The addition of crosslinkers introduces a covalent network structure into these polymers, which imparts programmable shape-memory effects.

SUMMARY OF THE INVENTION

The present invention includes a trifunctional crosslinker having the following general formula, in which W is selected from a group consisting of $CH_3C$, N, P=O, or $BO_3$, with R being selected from a group consisting of F, Cl, $CF_3$, or $CH_3$ and the amine groups being located meta or para with respect to R:

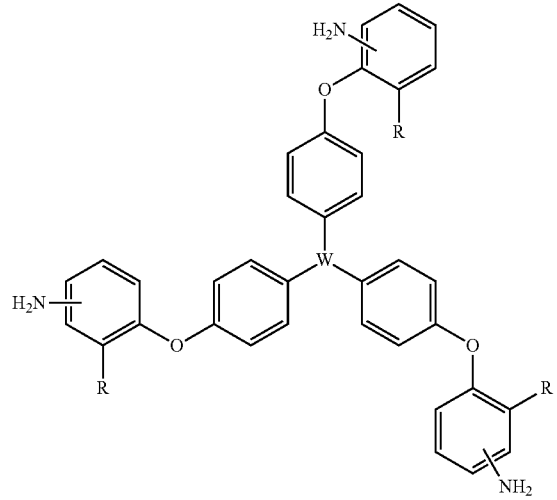

The present invention further includes a method for synthesizing the trifunctional crosslinker in which W is $CH_3C$ comprising the steps of: mixing a tris(hydroxyphenyl) compound, a halogenated nitrobenzene, and potassium carbonate in a polar solvent to form a tris(nitrophenoxy)phenyl compound; and reducing the tris(nitrophenoxy)phenyl compound by catalytic hydrogenation in the presence of 5% palladium on activated carbon in a hydrogen atmosphere to form a tris(aminophenoxy)phenyl compound. In one exemplary embodiment, the tris(aminophenoxy)phenyl compound is 1,1,1-tris[4-(4-aminophenoxy)phenyl]ethane.

The present invention further includes a method for synthesizing the trifunctional crosslinker in which W is P=O comprising the steps of: oxidizing a tris(methoxyphenyl) phosphine compound with aqueous hydrogen peroxide to form a tris(methoxyphenyl)phosphine oxide compound;

demethylating the tris(methoxyphenyl)phosphine oxide compound by heating in pyridine hydrochloride to form a tris(hydroxyphenyl) compound; mixing the tris(hydroxyphenyl) compound, a halogenated nitrobenzene, and potassium carbonate in a polar solvent to form a tris(nitrophenoxy) phenyl compound; and reducing the tris(nitrophenoxy)phenyl compound by catalytic hydrogenation in the presence of 5% palladium on activated carbon in a hydrogen atmosphere to form a tris(aminophenoxy)phenyl compound. In one exemplary embodiment, the tris(aminophenoxy)phenyl compound is tris[(4-aminophenoxy)phenyl]phosphine oxide.

The present invention further includes a method for synthesizing the trifunctional crosslinker in which W is selected from the group consisting of N and $BO_3$, the method comprising the steps of: treating a tris(methoxyphenyl) compound with a demethylating medium to form a tris(hydroxyphenyl) compound, wherein the tris(methoxyphenyl) compound is selected from the group consisting of a tris(methoxyphenyl)amine compound or a tris(methoxyphenyl)borate compound and wherein the demethylating medium is selected from the group consisting of pyridine hydrochloride or aqueous HBr; mixing the tris(hydroxyphenyl) compound, a halogenated nitrobenzene, and potassium carbonate in a polar solvent to form a tris(nitrophenoxy)phenyl compound; and reducing the tris(nitrophenoxy)phenyl compound by catalytic hydrogenation in the presence of 5% palladium on activated carbon in a hydrogen atmosphere to form a tris(aminophenoxy)phenyl compound.

DETAILED DESCRIPTION OF THE INVENTION

Figure 1:
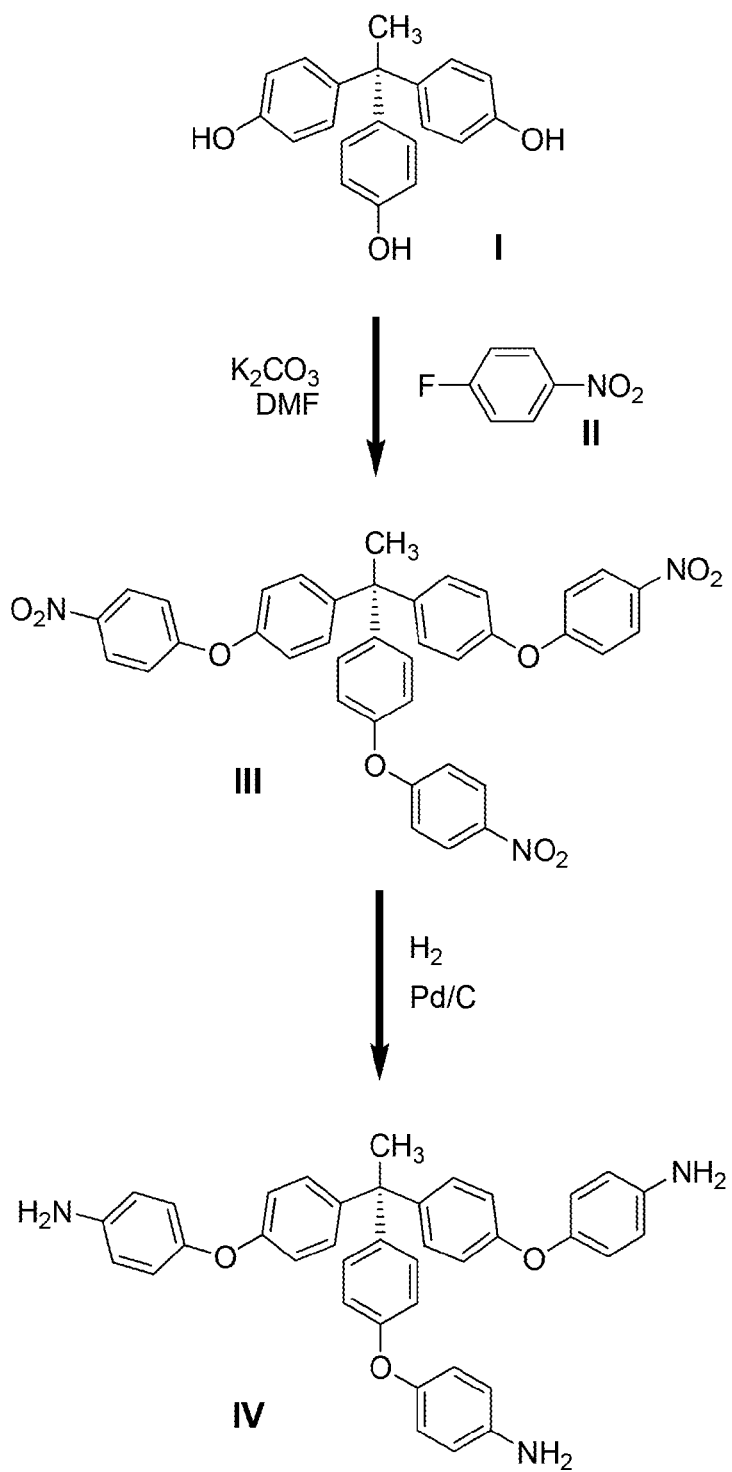
FIG. 1 illustrates the synthesis of an exemplary triamine crosslinker 1,1,1-tris[4-(4-aminophenoxy)phenyl]ethane (TAPE, IV) having the general structure A (W is $CH_3C$).

The present invention relates to multi-amine compounds that may be used to crosslink polyimides, polyamides, and poly(amide-imides) to create a covalent network structure that results in shape memory effects at elevated temperatures. The tetrahedral geometry and diphenylether linking groups of the presently disclosed tri- and tetrafunctional amine crosslinkers allow the synthesis of crosslinked polymers with both high-temperature tolerance and conformational flexibility. The present invention further includes methods of making the trifunctional amine crosslinkers.

The synthesis of a polyimide is typically accomplished by polymerization of a diamine and a dianhydride in a 1:1 molar ratio to generate a poly(amic acid) precursor, which is then converted to the corresponding polyimide typically by either thermal cure (heating to >200° C. in solution or solid state) or chemical imidization using a dehydrating agent or promoter such as acetic anhydride/triethylamine or acetic anhydride/pyridine. To generate a polyimide having the desired amount of crosslinking, an anhydride-terminated poly(amic acid) precursor is first generated by off-setting the dianhydride:diamine ratio so that the amount of dianhydride is in excess to cap both ends of the poly(amic acid) precursor. An appropriate amount of a multifunctional amine crosslinker is then be added to the precursor solution so that all the terminal anhydride groups will be consumed. Crosslinked polyimides may then be created using appropriate imidization conditions.

The synthesis of a polyamide is typically accomplished by two general methods. The first method involves polymerization of a diamine and a diacid chloride in a 1:1 molar ratio in an amide solvent such as N,N-dimethylformamide (DMF), N,N-dimethylacetamide (DMAc), N-methylpyrrolidone (NMP), etc. To generate a polyamide having the desired amount of crosslinking, an acid-chloride-terminated polymer is first generated by off-setting the diacid chloride:diamine ratio so that the amount of diacid chloride is in excess to cap both ends of the polymer. Subsequent addition of a multifunctional amine crosslinker in appropriate amounts to the acid-chloride-terminated polymer so that all the terminal acid chloride groups are consumed, immediately followed by casting and thermal curing under reduced pressure, leads to the crosslinked polyamide films.

The second method of synthesizing a polyamide involves polymerization of a diamine and a dicarboxylic acid with the aid of a promoter/catalyst combination such as triethylphosphite/pyridine (via Yamazaki-Higashi reaction) in an amide solvent such as N,N-dimethylformamide (DMF), N,N-dimethylacetamide (DMAc), N-methylpyrrolidone (NMP), etc. To generate a polyamide having the desired amount of crosslinking, a carboxylic acid-terminated polymer is first generated by off-setting the diacid:diamine ratio so that the amount of diacid monomer is in excess to cap both ends of the polymer. After the carboxylic acid-terminated polyamide into precipitated into water, it is washed (water & methanol) and dried. It is then redissolved in an amide solvent and mixed with an amide solution of a multifunctional amine crosslinker in appropriate amounts so that all the terminal carboxylic-acid groups are consumed, which is immediately followed by casting and thermal curing under reduced pressure to create crosslinked polyamide films.

The synthesis of a poly(amide-imide) is typically accomplished by polymerization of a diamine and a trimellitic anhydride (TMA) or a dicarboxylic acid monomer derived from trimellitic anhydride aided by triethylphosphite/pyridine (Yamazaki-Higashi reagent) in a 1:1 molar ratio in an amide solvent such as N,N-dimethylformamide (DMF), N,N-dimethylacetamide (DMAc), N-methylpyrrolidone (NMP) etc. To generate a poly(amide-imide) having the desired amount of crosslinking, it is more suitable that a carboxylic acid-terminated poly (amide-imide) is first generated via Yamazaki-Higashi reaction by off-setting diacid:diamine ratio so that the amount of diacid monomer is in excess to cap both ends of the polymer. After the carboxylic acid-terminated polyamide into precipitated into water, it is washed (water & methanol) and dried. It is then redissolved in an amide solvent and mixed with an amide solution of a multifunctional amine crosslinker in appropriate amounts so that all the terminal carboxylic-acid groups are consumed, which is immediately followed by casting and thermal curing under reduced pressure to create crosslinked poly(amide-imide) films.

A triamine crosslinker according to the present invention exhibits the following general formula A, in which W is CH$_3$C (methylcarbyl), N (trivalent nitrogen), P=O (phosphine oxide), or BO$_3$ (borate); R is H, F, Cl, CF$_3$, or CH$_3$; and the amine groups (NH$_2$) may be in the meta or para position with respect to R:

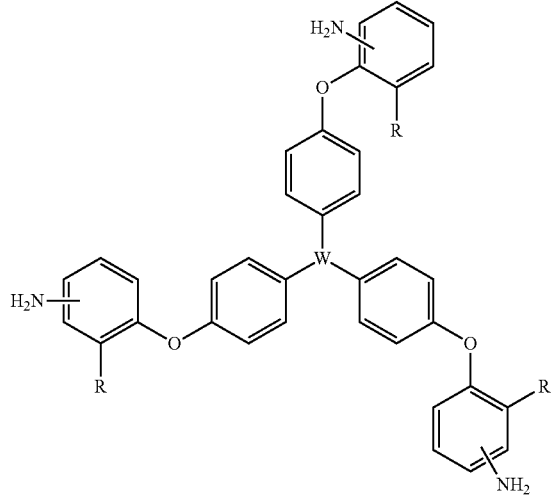

A

In one embodiment, a tetraamine crosslinker according to the present invention exhibits the following general formulas B or C, in which X is C or Si:

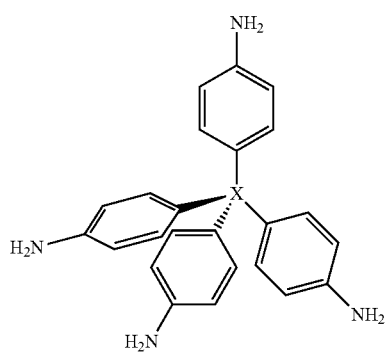

B

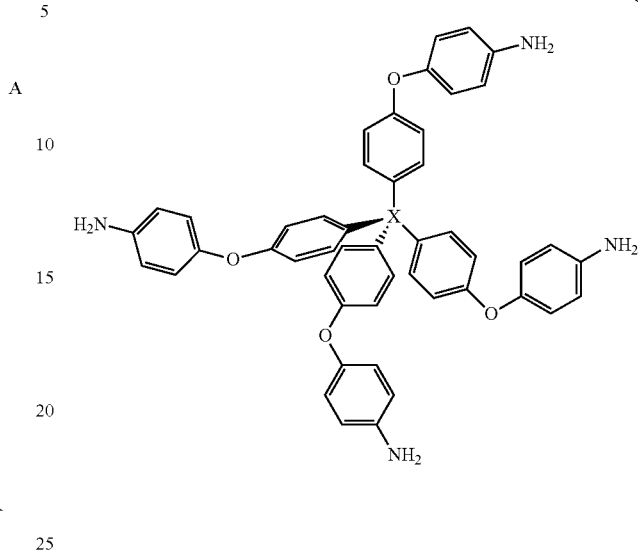

C

In another embodiment, a tetraamine crosslinker according to the present invention exhibits the following general formula D, in which Y is >C=O, —C(CF$_3$)$_2$—, —SO$_2$—, or —O—:

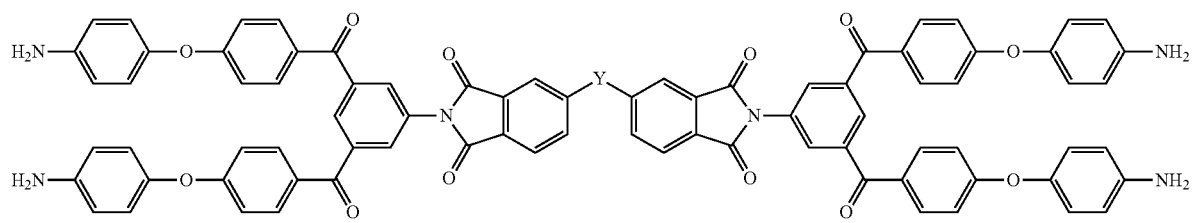

D

The present invention further includes methods of synthesizing triamine crosslinkers having the general structure A comprising the general steps of mixing a tris(hydroxyphenyl) compound, a halogenated nitrobenzene, and potassium carbonate in a polar solvent to form a tris(nitrophenoxy)phenyl compound; and reducing the tris(nitrophenoxy)phenyl compound by catalytic hydrogenation in the presence of 5% palladium on activated carbon in a hydrogen atmosphere to form a tris(aminophenoxy)phenyl compound.

Where W is P=O, the method further comprises oxidizing a tris(methoxyphenyl)phosphine compound with aqueous hydrogen peroxide to form a tris(methoxyphenyl)phosphine oxide compound; and demethylating the tris(methoxyphenyl)phosphine oxide compound by heating in pyridine hydrochloride to form the tris(hydroxyphenyl) compound.

Where NV is N or BO$_3$, the method further comprises treating a tris(methoxyphenyl) compound such as a tris(methoxyphenyl)amine compound or a tris(methoxyphenyl)borate compound with a demethylating medium such as pyridine hydrochloride or aqueous hydrogen bromide (HBr) to form the tris(hydroxyphenyl) compound. The HBr solution may be, for example, 48 wt % HBr.

The following examples and methods are presented as illustrative of the present invention or methods of carrying out

Example 1

Synthesis of TNPE

The following is an exemplary procedure for the synthesis of 1,1,1-tris[4-(4-nitrophenoxy)phenyl]ethane (TNPE, III) as depicted in FIG. 1. 1,1,1-tris(4-hydroxyphenyl)ethane (THPE, I) (10.0 g, 33.0 mmol), 1-fluoro-4-nitrobenzene (II) (15.4 g, 109 mmol), potassium carbonate (15.1 g, 109 mmol), and DMF (100 mL) were placed into a 250 mL three-necked flask equipped with a magnetic stir bar and nitrogen inlet and outlet. The mixture was stirred at room temperature for 24 hours and filtered. The filtrate was diluted with ethyl acetate (400 mL), and the organic layer was separated. The organic layer was washed with water three times. It was then dried over anhydrous magnesium sulfate and filtered. The filtrate was concentrated to 75 mL on a rotary evaporator and stored in a refrigerator for several days to afford 11.2 g (51%) of off-white crystals, m.p. 98-99° C. MS (m/e): 669 ($M^+$). Anal. Calcd. for $C_{38}H_{27}N_3O_9$: C, 68.18%; H, 4.06%; N, 6.27%; O, 21.50%. Found: C, 67.69%; H, 4.26%; N, 6.21%; O, 21.22%. FT-IR (KBr, $cm^{-1}$): 3076, 2979, 1586, 1513, 1486, 1344, 1248, 1165, 1107, 874, 846. $^1$H-NMR (DMSO-$d_6$, δ in ppm): 2.26 (s, 3H, $CH_3$), 7.17-7.27 (m, 18H, Ar—H), 8.28-8.31 (d, 6H, Ar—H).

Example 2

Synthesis of TAPE

The following is an exemplary procedure for the synthesis of an exemplary triamine crosslinker 1,1,1-tris[4-(4-aminophenoxy)phenyl]ethane (TAPE, IV) by reduction of TNPE (III) via catalytic hydrogenation as depicted in FIG. 1. TNPE (III) (5.0 g, 7.5 mmol), THF (50 mL), and 5% palladium on activated carbon (0.50 g) were added to a hydrogenation bottle. The bottle was secured on a Parr hydrogenation apparatus, flushed three times with hydrogen, and then pressurized to 55 psi. After the mixture had been agitated at room temperature for 24 hours under the hydrogen pressure of 55 psi, it was filtered through Celite. The filter cake was washed with THF, and then the filtrate was evaporated to dryness on a rotary evaporator to afford a 4.25 g (98%) of yellow crystal, which was used without further purification, m.p. 220-22 1° C. MS (m/e): 579 ($M^+$). Anal. Calcd. for $C_{38}H_{33}N_3O_3$: C, 78.73%; H, 5.74%; N, 7.25%. Found: C, 78.17%; H, 5.78%; N, 7.04%. FT-IR (KBr, $cm^{-1}$): 3441, 3361 ($NH_2$), 3035, 2970, 1617, 1581, 1497, 1384, 1232, 1173, 1117, 1010, 871, 842. $^1$H-NMR (DMSO-$d_6$, δ in ppm): 2.02 (s, 3H, $CH_3$), 4.99 (s, 6H, $NH_2$), 6.53-6.58 (d, 6H, Ar—H), 6.68-6.74 (m, 12H, Ar—H), 6.88-6.93 (d, 6H, Ar—H).

Example 3

Synthesis of TMPO

Figure 2:
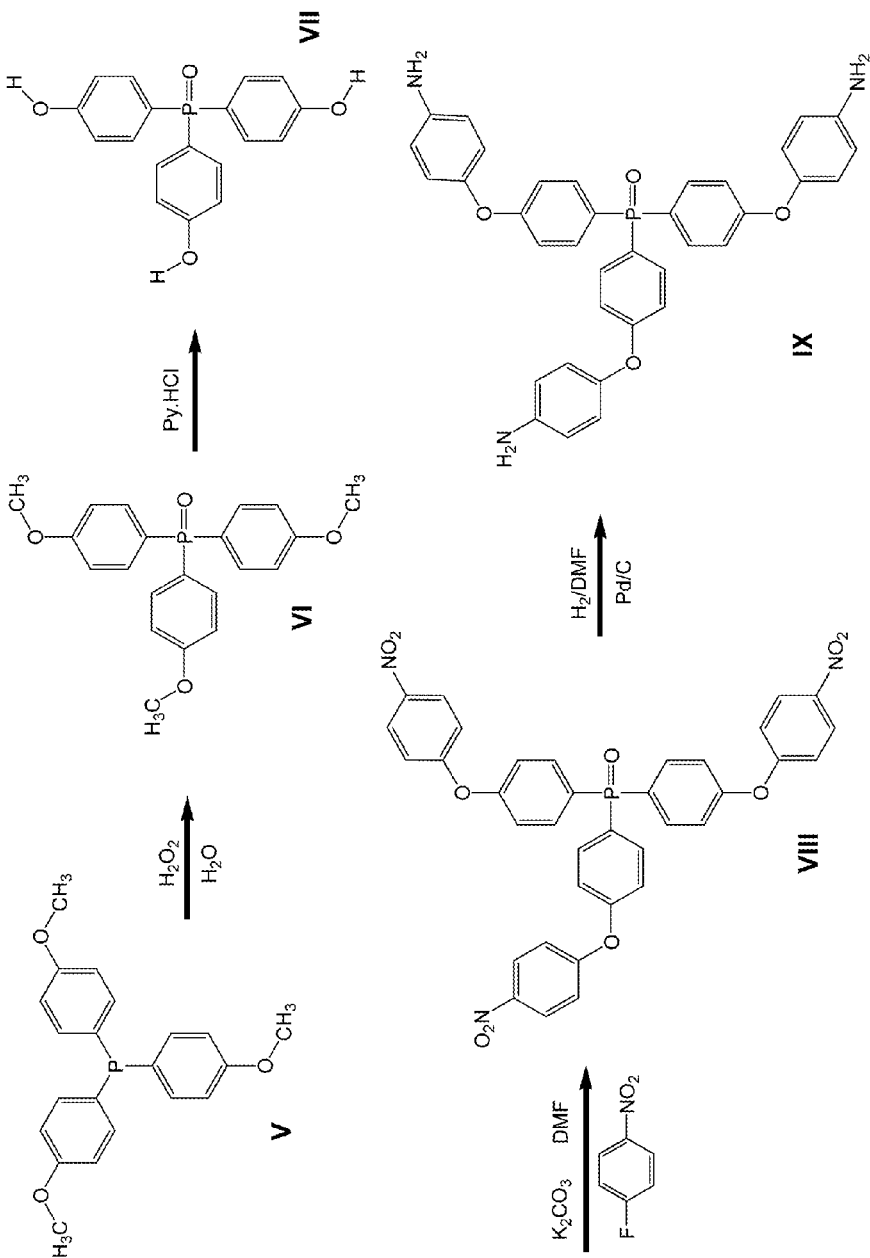
FIG. 2 illustrates the synthesis of another exemplary triamine crosslinker tris[(4-aminophenoxy)phenyl]phosphine oxide (TNPO, IX) having the general structure A (W is P=O).

The following is an exemplary procedure for the synthesis of tris(4-methoxyphenyl)phosphine oxide (TMPO, VI) as depicted in FIG. 2. Into a 100 mL three-necked flask equipped with a magnetic stir bar and nitrogen inlet and outlet were placed tris(4-methoxyphenyl)phosphine (TMP, V) (3.0 g, 8.5 mmol) and acetone (30 mL). A mixture of water (2 mL) and $H_2O_2$ (35%, 1 mL, 9 mmol) was added slowly. After the mixture had been stirred at room temperature for 1 hour, the acetone was evaporated, and methylene chloride (50 mL) was added. The organic phase was washed with a saturated NaCl solution (35 mL) three times with the aid of a separatory funnel. The organic layer was then dried over anhydrous sodium sulfate. Finally, the solvent was removed via rotary evaporation to afford 3.0 g (95%) of a white solid, m.p. 144.7-145.4° C. MS (m/e): 368 ($M^+$). Anal. Calcd. for $C_{21}H_{21}O_4P$: C, 68.47%; H, 5.75%; P, 8.41%. Found: C, 68.42%; H, 5.72%; P, 8.11%. FT-IR (KBr, $cm^{-1}$): 3068, 3026, 2959, 2837, 1597, 1569, 1503, 1468, 1289, 1254, 1179, 1121, 1019, 803, 671, 543. $^1$H-NMR (CDCl$_3$, δ in ppm): 3.84 (s, 6H, $CH_3$), 6.94-6.97 (dd, 6H, Ar—H), 7.54-7.60 (dd, 6H, Ar—H). $^{13}$C-NMR (DMSO-$d_6$, δ in ppm): 55.29, 114.08, 114.21, 124.19, 125.28, 133.21, 133.32, 161.79, 161.82.

Example 4

Synthesis of THPO

The following is an exemplary procedure for the synthesis of tris(4-hydroxyphenyl)phosphine oxide (THPO, VII) via demethylation of TMPO (VI) as depicted in FIG. 2. Into a 500 mL three-necked flask equipped with a magnetic stir bar and nitrogen inlet and outlet were placed TMPO (VI) (25.0 g, 67.9 mmol) and an excess of pyridine hydrochloride (250 g) at 210° C. for 2 hours. The light brown solution was poured into water while it was still hot. The white precipitate was collected and recrystallized from ethyl acetate to afford 21.0 g (95%) of white crystals, m.p. 274.8-276.8° C. MS (m/e): 326 ($M^+$). FT-IR (KBr, $cm^{-1}$): 3380, 1601, 1581, 1505, 1436, 1278, 1175, 1119, 1068, 831, 677, 537. $^1$H-NMR (DMSO-$d_6$, δ in ppm): 6.86-6.89 (dd, 6H, Ar—H), 7.32-7.38 (dd, 6H, Ar—H), 10.14 (s, 3H, OH). $^{13}$C-NMR (DMSO-$d_6$, δ in ppm): 115.32, 115.45, 122.59, 123.69, 133.29, 133.40, 160.28, 160.30.

Example 5

Synthesis of TNPO

The following is an exemplary procedure for the synthesis of tris[(4-nitrophenoxy)phenyl]phosphine oxide (TNPO, XIII) as depicted in FIG. 2. Into a 250 mL three-necked flask equipped with a magnetic stir bar and nitrogen inlet and outlet were placed THPO (VII) (7.52 g, 20.0 mmol), 1-fluoro-4-nitrobenzene (II) (9.32 g, 66.0 mmol), potassium carbonate (9.14 g, 66.0 mmol), and DMF (100 mL) at 100° C. for 48 hours. The mixture was allowed to cool to room temperature and filtered. The filtrate was poured into water, and the precipitate was extracted with ethyl acetate (300 mL) three times with the aid of a separatory funnel. The combined organic extract was concentrated under vacuum, and 13.3 g (97%) of yellow crystals that were formed during the concentrating process was collected by filtration, m.p. 205.0-206.6° C. MS (m/e): 689 ($M^+$). FT-IR (KBr, $cm^{-1}$): 3071, 1612, 1585, 1523, 1487, 1345, 1242, 1176, 1116, 879, 866, 831, 788, 696, 556. $^1$H-NMR (DMSO-$d_6$, δ in ppm): 7.27-7.31 (d, 6H, Ar—H), 7.35-7.37 (d, 6H, Ar—H), 7.75-7.80 (m, 6H, Ar—H), 8.27-8.31 (d, 6H, Ar—H). $^{13}$C-NMR (DMSO-$d_6$, δ in ppm): 118.84, 119.82, 119.94, 126.22, 128.18, 129.23, 134.09, 134.20, 143.09, 157.93, 157.96, 161.29.

Example 6

Synthesis of TAPO

The following is a procedure for the synthesis of another exemplary triamine crosslinker tris[(4-aminophenoxy)phenyl]phosphine oxide (TAPO, XIV) having the general structure A where W is P=O (IUPAC name 4,4',4"-(4,4',4"-phosphinetriyltris(benzene-4,1-diyl)tris(oxy))trianiline) by reduction of TNPO (XIII) via catalytic hydrogenation as depicted in FIG. 2. TNPO (VIII) (8.0 g, 11.6 mmol), DMF (120 mL), and 5% palladium on activated carbon (0.50 g) were added to a hydrogenation bottle. The bottle was secured on a Parr hydrogenation apparatus, flushed three times with hydrogen, and then pressurized to 60 psi. After the mixture had been agitated at room temperature for 24 hours under the hydrogen pressure of 60 psi, it was filtered through a cake of Celite. The filter cake was washed with DMF. The filtrate was then poured into water to precipitate a white solid that was subsequently recrystallized from ethanol/water to afford 6.41 g (98%) of white crystal, m.p. 211.1-211.5° C. MS (m/e): 559 (M). Anal. Calcd. for $C_{36}H_{30}N_3O_4P$: C, 72.11%; H, 5.04%; N, 7.01%. Found: C, 72.01%; H, 4.97%; N, 6.91%. FT-IR (KBr, $cm^{-1}$): 3437, 3328, 3210, 3042, 1592, 1507, 1493, 1242, 1197, 1165, 1117, 871, 830, 671, 577. $^1$H-NMR (DMSO-$d_6$, δ in ppm): 5.06 (s, 6H, $NH_2$), 6.59-6.62 (d, 6H, Ar—H), 6:79-6.81 (d, 6H, Ar—H), 6.94-6.96 (d, 6H, Ar—H), 7.48-7.53 (d, 6H, Ar—H). $^{13}$C-NMR (DMSO-$d_6$, δ in ppm): 114.85, 115.89, 116.01, 121.34, 125.06, 126.13, 133.40, 133.51, 144.11, 146.13, 162.89, 161.92.

Example 7

Synthesis of a Crosslinked Polyimide

The following exemplary procedure demonstrates the utility of the presently disclosed triamine crosslinkers for the synthesis of crosslinked polyimide films. An exemplary fluorinated polyimide, CP2 (LaRC™-CP2, NASA Langley Research Center), was prepared by adding 1,3-bis(3-aminophenoxy)benzene (1.081 g, 3.700 mmol) and DMAc (14 mL) to a 50 mL three-necked flask equipped with a magnetic stirrer and a nitrogen inlet and outlet and stirred under dry nitrogen at room temperature for 30 minutes. An excess of 2,2-bis(phthalic anhydride)-1,1,1,3,3,3-hexafluoroisopropane (1.777, 4.000 mmol) was then introduced to the resulting solution. The light yellow solution was agitated at room temperature for 24 hours to afford a solution of poly(amic acid) oligomers (PAA oligomers). TAPE (IV) (0.1159 g, 0.200 mmol, 5 mol %) synthesized according to FIG. 1 and Examples 1 and 2 was added to the solution of PAA oligomers in DMAc. After the TAPE had completely dissolved, the resulting PAA sol-gel precursor solution was poured into a glass petri dish, followed by vacuum evaporation of the DMAc at 50° C. and heat-treatment according to following schedule: 100° C./2 hours, 150° C./2 hours, 175° C./1 hour, 200° C./2 hours, 250° C./1 hour, and 300° C./1 hour to form films consisting of xE-CP2 (IX). The resulting crosslinked polyimide films were approximately 20-100 μM in thickness. As compared to the $T_g$ of about 219° C. for neat polyimide (CP2, data not shown), the crosslinked CP2 films comprising 5 mol % TAPE demonstrated a higher $T_g$ of about 239° C.

Although this invention has been described with respect to certain preferred embodiments, various other embodiments and various changes and modifications to the disclosed embodiment(s) will become apparent to those skilled in the art. All such other embodiments, changes, and modifications are intended to come within the spirit and scope of the appended claims.

What is claimed is:

1. A trifunctional crosslinker having the general formula:

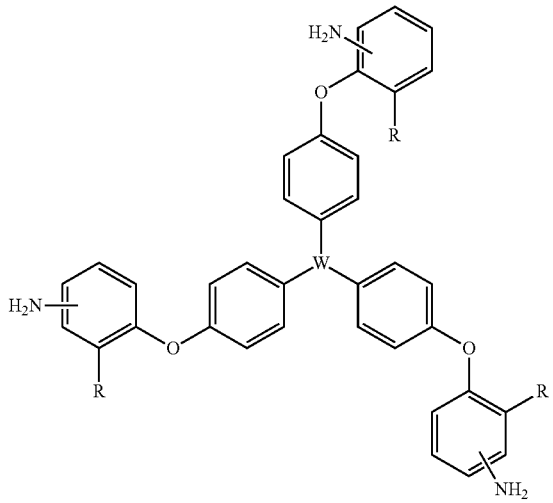

wherein W is selected from a group consisting of $CH_3C$, N, P=O, or B(—O)$_3$; R is F, Cl, or $CH_3$ when W is $CH_3C$ and R is H, F, Cl, $CF_3$, or $CH_3$ when W is N, P=O, or B(—O)$_3$; and the amine groups are located meta or para with respect to R.

* * * * *